(12) United States Patent
Struck et al.

(10) Patent No.: US 9,753,039 B2
(45) Date of Patent: *Sep. 5, 2017

(54) PROGNOSIS OF ADVERSE EVENTS IN PATIENTS WITH SUSPECTED CHRONIC HEART FAILURE

(71) Applicant: B.R.A.H.M.S. GmbH, Hennigsdorf (DE)

(72) Inventors: Joachim Struck, Berlin (DE); John GF Cleland, Yorkshire (GB)

(73) Assignee: B.R.A.H.M.S GmbH, Hennigsdorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/211,802

(22) Filed: Jul. 15, 2016

(65) Prior Publication Data

US 2016/0320411 A1 Nov. 3, 2016

Related U.S. Application Data

(63) Continuation of application No. 14/391,953, filed as application No. PCT/EP2013/057626 on Apr. 11, 2013.

(30) Foreign Application Priority Data

Apr. 12, 2012 (EP) .................... 12163921

(51) Int. Cl.
G01N 31/00 (2006.01)
G01N 33/53 (2006.01)
G01N 33/68 (2006.01)

(52) U.S. Cl.
CPC ......... *G01N 33/68* (2013.01); *G01N 33/6893* (2013.01); *G01N 2333/585* (2013.01); *G01N 2800/325* (2013.01); *G01N 2800/50* (2013.01); *G01N 2800/54* (2013.01); *G01N 2800/56* (2013.01)

(58) Field of Classification Search
None
See application file for complete search history.

(56) References Cited

U.S. PATENT DOCUMENTS

| 7,723,492 | B2 | 5/2010 | Bergmann | |
| 8,354,506 | B2 * | 1/2013 | Bergmann | ............. C07K 16/26 530/387.1 |
| 8,465,941 | B2 * | 6/2013 | Bergmann | ............. G01N 33/74 435/15 |
| 2010/0047835 | A1 | 2/2010 | Bergmann et al. | |
| 2011/0117589 | A1 | 5/2011 | Bergmann et al. | |
| 2015/0247871 | A1 | 9/2015 | Bergmann et al. | |

FOREIGN PATENT DOCUMENTS

| WO | 2008/040328 A2 | 4/2008 |
| WO | 2009112307 A1 | 9/2009 |
| WO | 2010/118855 A1 | 10/2010 |

OTHER PUBLICATIONS

Maisel, Alan S. et al., "Biomarkers in acute heart failure—state of the art", XP009171202—Nature Reviews, Cardiology—Aug. 2012, vol. 9., No. 8, pp. 478-490.
International Search Report and Written Opinion corresponding to PCT/EP20131057626—Date of Completion: Jul. 19, 2013—Date of Mailing: Jul. 25, 2013.

* cited by examiner

*Primary Examiner* — Lisa Cook
(74) *Attorney, Agent, or Firm* — Millen White Zelano and Branigan, PC; Csaba Henter; Anthony Zelano (57) ABSTRACT

The present invention is in the field of clinical diagnostics. Particularly the present invention relates to the prognosis of adverse events in patients with stable chronic heart failure or being suspected of having stable chronic heart failure by determination of the level of Procalcitonin (PCT).

20 Claims, 5 Drawing Sheets

SEQUENCE LISTING

<160> NUMBER OF SEQ ID NOS: 3

<210> SEQ ID NO 1
<211> LENGTH: 116
<212> TYPE: PRT
<213> ORGANISM: Homo sapiens

<400> SEQUENCE: 1

```
Ala Pro Phe Arg Ser Ala Leu Glu Ser Ser Pro Ala Asp Pro Ala Thr
 1               5                  10                  15

Leu Ser Glu Asp Glu Ala Arg Leu Leu Leu Ala Ala Leu Val Gln Asp
                20                  25                  30

Tyr Val Gln Met Lys Ala Ser Glu Leu Glu Gln Glu Gln Glu Arg Glu
            35                  40                  45

Gly Ser Ser Leu Asp Ser Pro Arg Ser Lys Arg Cys Gly Asn Leu Ser
        50                  55                  60

Thr Cys Met Leu Gly Thr Tyr Thr Gln Asp Phe Asn Lys Phe His Thr
65                  70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
                100                 105                 110

Gln Asn Ala Asn
        115
```

<210> SEQ ID NO 2
<211> LENGTH: 76
<212> TYPE: PRT
<213> ORGANISM: Homo sapiens

<400> SEQUENCE: 2

```
His Pro Leu Gly Ser Pro Gly Ser Ala Ser Asp Leu Glu Thr Ser Gly
 1               5                  10                  15

Leu Gln Glu Gln Arg Asn His Leu Gln Gly Lys Leu Ser Glu Leu Gln
                20                  25                  30

Val Glu Gln Thr Ser Leu Glu Pro Leu Gln Glu Ser Pro Arg Pro Thr
            35                  40                  45

Gly Val Trp Lys Ser Arg Glu Val Ala Thr Glu Gly Ile Arg Gly His
        50                  55                  60

Arg Lys Met Val Leu Tyr Thr Leu Arg Ala Pro Arg
65                  70                  75
```

<210> SEQ ID NO 3
<211> LENGTH: 32
<212> TYPE: PRT
<213> ORGANISM: Homo sapiens

<400> SEQUENCE: 3

```
Ser Pro Lys Met Val Gln Gly Ser Gly Cys Phe Gly Arg Lys Met Asp
 1               5                  10                  15

Arg Ile Ser Ser Ser Ser Gly Leu Gly Cys Lys Val Leu Arg Arg His
                20                  25                  30
```

PROGNOSIS OF ADVERSE EVENTS IN PATIENTS WITH SUSPECTED CHRONIC HEART FAILURE

This application is a continuation of application Ser. No. 14/391,953, filed on Oct. 10, 2014, now U.S. Pat. No. 9,488,659, issued on Nov. 8, 2016, which is a 371 of international PCT/EP2013/057626, filed on Apr. 11, 2013.

FIELD OF THE INVENTION

The present invention is in the field of clinical diagnostics. Particularly the present invention relates to the prognosis of adverse events (e.g. mortality) in patients with stable chronic heart failure or being suspected of having stable chronic heart failure by determination of the level of Procalcitonin (PCT).

BACKGROUND OF THE INVENTION

Procalcitonin (PCT) has become a well-established biomarker for the diagnosis of sepsis. PCT reflects the severity of a bacterial infection and is in particular used to monitor progression of infection into sepsis, severe sepsis, or septic shock. It is possible to use PCT to measure the activity of the infection-associated systemic inflammatory response, to control success of antibacterial therapy, and to estimate prognosis (Assicot et al. 1993. *Lancet* 341:515-8; Clec'h C et al. 2004. *Crit Care Med* 32:1166-9; Lee et al. 2004;. *Yonsei Med J* 45:29-37; Meisner et al. 2005. *Curr Opin Crit Care* 11:473-480; Wunder et al. 2004. *Inflamm Res* 53: 158-163). The increase of PCT levels in patients with sepsis correlates with mortality (Oberhoffrer et al. 1999. *Clin Chem Lab Med* 37:363-368).

During bacterial infections, plasma PCT concentrations are typically above 0.25 ng/mL. Recently, it has been found that in several non-infectious diseases, like coronary artery disease or acute coronary syndromes, PCT concentrations can be elevated above the normal range but below the concentrations, which have been known so far to be associated with bacterial infections requiring antibacterial treatment, and that these PCT concentrations are associated with a prognosis of adverse events in these patients (Sinnig et al. 2011. *Circ J* 75:1184-1191; Kelly et al. 2010. *Biomarkers* 15:325-331).

Patent applications EP 07015271.5 and EP 09719129.0 disclose the use of PCT in the risk stratification of patients suffering from stable coronary artery disease (CAD) and acute coronary syndromes (ACS), respectively.

Heart failure (HF), also termed congestive heart failure (CHF) is a cardiac condition that occurs when a problem with the structure or function of the heart impairs its ability to supply sufficient blood flow to meet the body's needs. It can cause a large variety of symptoms, particularly shortness of breath (SOB) at rest or during exertion and/or fatigue, signs of fluid retention such as pulmonary congestion or ankle swelling, and objective evidence of an abnormality of the structure or function of the heart at rest. However, some patients can be completely symptom free and asymptomatic structural or functional abnormalities of the heart are considered as precursors of symptomatic heart failure and are associated with high mortality (Wang et al. 2003. *Circulation* 108: 977-82). Heart failure is a common disease: more than 2% of the U.S. population, or almost 5 million people, are affected and 30 to 40% of patients die from heart failure within 1 year after receiving the diagnosis (McMurray J. J., Pfeffer M. A. 2005. *Lancet* 365: 1877-89). Heart failure is often undiagnosed due to a lack of a universally agreed definition and challenges in definitive diagnosis, particularly in the early stage. With appropriate therapy, heart failure can be managed in the majority of patients, but it is a potentially life threatening condition, and progressive disease is associated with an overall annual mortality rate of 10%. It is the leading cause of hospitalization in people older than 65 years (Haldemann G. A. et al. 1999. *Am Heart J* 137: 352-60). As a consequence, the management of heart failure consumes 1-2% of total health-care expenditure in European countries (Berry et al. 2001. *Eur J Heart Fail* 3: 749-53).

Chronic heart failure (chronic HF) is a long-term condition developing over months and years with a usually stable treated symptomatology. This condition is associated with the heart undergoing adaptive responses which, however, can be deleterious in the long-term and lead to a worsening condition. Acute heart failure (AHF) is a term used to describe exacerbated or decompensated heart failure, referring to episodes in which a patient can be characterized as having a change in heart failure signs and symptoms resulting in a need for urgent therapy or hospitalization. AHF develops rapidly during hours or days and can be immediately life threatening because the heart does not have time to undergo compensatory adaptations. Chronic HF may also decompensate which most commonly result from an intercurrent illness (such as pneumonia), myocardial infarction, arrhythmias, uncontrolled hypertension, or a patient's failure to maintain a fluid restriction, diet or medication.

Miller et al. examined in a cohort of patients with chronic HF hospitalized for decompensation of HF, the use of PCT for an intermediate-term prognosis of post-hospital cardiovascular mortality (mean follow-up 10 months) (Miller et al 2009. *J Cardiovasc Trans Res* 2:526-535). However, procalcitonin levels were not different between non-survivors and survivors. In contrast, PCT levels tended to be higher in survivors than in non-survivors. Maisel et al. reported that the level of PCT was significantly associated with the prognosis of short-term (90-days) all-cause mortality in patients diagnosed with acute heart failure (Maisel et al. 2012. *Eur J Heart Fail,* 14:278-286).

A method for the diagnosis of infections of the airways and lungs with associated heart failure is described in EP 07817601.3.

However, it is unknown whether relatively elevated PCT concentrations in patients with stable chronic heart failure or patients suspected of having stable chronic heart failure can be associated with the prognosis of an adverse event (e.g. mortality). The possibility of predicting adverse events at presentation of the patient is important, since early recognition of risk is a prerequisite for initiating measures helping to prevent the development of adverse events.

It has thus been the task of the present invention to investigate whether PCT levels in patients with stable chronic heart failure or patients suspected of having stable chronic heart failure are associated with the prognosis of adverse events (e.g. mortality).

SUMMARY OF THE INVENTION

The present invention relates to an in vitro method for the prognosis of adverse events (e.g. mortality) in a patient with stable chronic heart failure or being suspected of having stable chronic heart failure comprising determining the level of procalcitonin (PCT) or fragments thereof in a sample from said patient and correlating the level of PCT or fragments thereof to the risk of getting an adverse event (e.g. mortality).

DETAILED DESCRIPTION OF THE INVENTION

The present invention relates to an in vitro method for the prognosis of adverse events (e.g. mortality) in a patient with stable chronic heart failure or being suspected of having stable chronic heart failure comprising determining the level of procalcitonin (PCT) or fragments thereof in a sample from said patient and correlating the level of PCT or fragments thereof to the risk of getting an adverse event (e.g. mortality).

In a preferred embodiment of the invention the level of PCT consisting of amino acids 1 to 116 or 2 to 116 or 3 to 116 of SEQ ID NO:1 is determined.

A further embodiment of the invention comprises determining the level of one or more additional prognostic marker in a sample obtained from said patient, and combining both said level of procalcitonin or fragments thereof and said level of one or more additional prognostic marker to said predisposition of getting an adverse event, whereby the combination of said level of procalcitonin or fragments thereof with said level of one or more additional prognostic markers increases the predictive value of said level of procalcitonin or fragments thereof for the prognosis of adverse events.

Further markers which may be used as additional prognostic marker(s) may be selected from the group comprising troponin, myeloperoxidase, C-reactive protein (CRP), neopterin, growth differentiation factor 15 (GDF15), interleukin 1 receptor-like 1 (ST2), cystatin-C, as well as the following peptides in form of their mature peptides, precursors, prohormones and associated prohormone fragments: atrial natriuretic peptide, adrenomedullin, endothelins, vasopressin.

In a further preferred embodiment one of said additional prognostic marker(s) is pre-proBNP or fragments thereof (these can be proBNP or derivatives thereof, i.e. type B natriuretic peptide (BNP) or N-terminal-proBNP (NT-proBNP), as described above) in a sample obtained from said patient.

In another more preferred embodiment said fragment of pre-proBNP is NT pro-BNP (SEQ ID NO:2).

In another more preferred embodiment said fragment of pre-proBNP is BNP (SEQ ID NO:3).

In a further embodiment, the in vitro method for the prognosis of getting an adverse event for a patient with stable chronic heart failure or being suspected of having stable chronic heart failure further comprises mathematically combining said level of procalcitonin or fragments thereof with the level of one or more additional prognostic marker, whereby the combination of said level of procalcitonin or fragments thereof with said level of additional prognostic marker(s) increases the predictive value of said level of procalcitonin or fragments thereof or the level of said related marker for getting an adverse event. The mathematical combination can be for instance an algorithm categorizing patients according to whether their level of procalcitonin is above or below a certain threshold value and whether their level of marker X (and Y, Z . . . ) is above or below a certain threshold value.

Another subject of the invention is the use of an ultrasensitive procalcitonin assay having a lower limit of detection of <0.045 (+/−0.010) ng/mL for determining a predisposition to an adverse event in a patient with stable chronic heart failure or being suspected of having stable chronic heart failure.

"Prognosis" relates to the prediction of an adverse event (e.g. mortality) for a patient with stable chronic heart failure or being suspected of having stable chronic heart failure. This may include an estimation of the chance of recovery or the chance of death for said patient.

Adverse event is defined as worsening or decompensation of heart failure, a cerebrovascular event, a cardiovascular event and mortality.

A cerebrovascular event is defined as ischemic stroke, hemorrhagic stroke or transient ischemic attack (TIA).

A cardiovascular event is defined as acute coronary syndrome including myocardial infarction.

Mortality is defined as cardiovascular death (attributable to e.g. myocardial ischemia and infarction, heart failure, cardiac arrest or cerebrovascular accident) and non-cardiovascular mortality (including all other causes of death, e.g. infection, malignancies).

Heart failure (HF), also termed congestive heart failure (CHF) is a cardiac condition that occurs when a problem with the structure or function of the heart impairs its ability to supply sufficient blood flow to meet the body's needs. Chronic heart failure is a long-term condition (months/years) usually with stable treated symptomatology, that is associated with the heart undergoing adaptive responses (e.g. dilation, hypertrophy) to a precipitating cause. These adaptive responses, however, can be deleterious in the long-term and lead to a worsening condition.

Patients with chronic HF can be grouped into stable, worsening and decompensated chronic HF patients (see Table 1, adapted according to ESC Guidelines 2008 [Dickstein et al. 2008. *Eur Heart J* 29:2388-2442]). Acute heart failure (AHF) is defined as the rapid onset of symptoms and signs secondary to abnormal cardiac function. AHF can present itself as acute de novo (new onset of acute heart failure in a patient without previously known cardiac dysfunction) or acute decompensation of chronic heart failure. Decompensation in chronic HF patients most commonly result from an intercurrent illness (such as pneumonia), myocardial infarction, arrhythmias, uncontrolled hypertension, or a patient's failure to maintain a fluid restriction, diet or medication. Chronic heart failure, which is worsening or decompensated, as well as AHF is characterized as having a change in HF signs and symptoms resulting in a need for urgent therapy or therapy adjustment and the requirement of hospitalization (Jessup et al. 2009. *Circulation* 119:1977-2016). Three clinical profiles describe these patients: 1) volume overload, manifested by pulmonary and/or systematic congestion, frequently precipitated by an acute increase in chronic hypertension; 2) profound depression of cardiac output manifested by hypotension, renal insufficiency, and/or a shock syndrome; and 3) signs and symptoms of both fluid overload and shock (Jessup et al. 2009. *Circulation* 119:1977-2016). After treatment, patients with AHF or acute decompensated chronic HF may return to a chronic stable compensated state. A comparison of features for acute and chronic stable heart failure is shown in table 2.

A patient having chronic stable heart failure or who is suspected of having chronic stable heart failure is characterized by
the presence of structural or functional failure of the heart that impairs its ability to supply sufficient blood flow to meet the body's needs,
the absence of volume overload (manifested by pulmonary and/or systematic congestion) and/or profound depression of cardiac output (manifested by hypotension, renal insufficiency and/or a shock syndrome),
and whereas the patient is not in need of urgent therapy or therapy adjustment and does not require hospitalization.
Common factors that precipitate hospitalization for heart failure are e.g. acute myocardial ischemia, noncompliance with the medical regimen (sodium and/or fluid restriction), uncorrected high blood pressure, atrial fibrillation and other arrhythmias, pulmonary embolus or concurrent infections (Jessup et al. 2009. *Circulation* 119:1977-2016).

In a preferred embodiment of the invention an adverse event occurring within 7 years, preferably within 5 years, more preferred within 4 years, most preferred within 2 years is predicted.

In another preferred embodiment of the invention the level of procalcitonin or fragments thereof is correlated with one or more clinical variables selected from a group comprising age, gender, diabetes, chronic obstructive pulmonary disease (COPD), symptoms, quality of life, New York Heart Association functional classification of heart failure category (NYHA), Body mass index (BMI), heart rate and rhythm, systolic and diastolic blood pressure, edema and severity of ventricular dysfunction.

The term "patient" as used herein refers to a living human or non-human organism that is receiving medical care or that should receive medical care due to a disease. This includes persons with no defined illness who are being investigated for signs of pathology. Thus the methods and assays described herein are applicable to both, human and veterinary disease.

The term "correlating", as used herein in reference to the use of PCT as prognostic marker, refers to comparing the presence or amount of the marker in a patient to its presence or amount in persons known to suffer from, or known to be at risk of, a given condition. A marker level in a patient sample can be compared to a level known to be associated with a specific prognosis. The sample's marker level is said to have been correlated with a prognosis; that is, the skilled artisan can use the marker level to determine whether the patient has a specific risk to suffer from an adverse event, and respond accordingly. Alternatively, the sample's marker level can be compared to a marker level known to be associated with a good outcome (e.g. a low risk to suffer from an adverse event).

The term "sample" as used herein refers to a sample of bodily fluid obtained for the purpose of diagnosis, prognosis, or evaluation of a subject of interest, such as a patient. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus, in a preferred embodiment of the invention the sample is selected from the group comprising a blood sample, a serum sample, a plasma sample, a cerebrospinal fluid sample, a saliva sample and a urine sample or an extract of any of the aforementioned samples. Preferably, the sample is a blood sample, most preferably a serum sample or a plasma sample.

According to the method, the patient with stable chronic heart failure or being suspected of having stable chronic heart failure has an increased risk of getting an adverse event (e.g. mortality) when said determined PCT level is higher than a predetermined threshold level. Preferably, the predetermined threshold level is between 0.015 and 0.05 ng/mL, more preferred between 0.015 ng/mL and 0.035 ng/mL, even more preferred between 0.015 ng/mL and 0.03 ng/mL, even more preferred between 0.015 ng/mL and 0.025 ng/mL, most preferred between 0.02 ng/mL and (below) 0.015 ng/mL. In a preferred embodiment the patient with stable chronic heart failure or being suspected of having stable chronic heart failure has an increased risk of getting an adverse event (e.g. mortality) when said determined PCT level is higher than 0.05 ng/mL, preferably higher than 0.035 ng/mL, more preferably higher than 0.03 ng/mL, even more preferably higher than 0.025 ng/mL, even more preferably higher than 0.02 ng/mL, most preferred higher than 0.015 ng/mL.

The PCT levels of the present invention have been determined with a PCT test format (BRAHMS KRYPTOR PCT sensitive), which has the same calibration in the quantitative measuring range as a more sensitive PCT Assay (BRAHMS PCT LIA sensitive), the latter being able to quantitatively determine PCT levels in the normal population, giving median PCT levels as described in EP 09011073.5 ("Procalcitonin for the prognosis of adverse events in the asymptomatic population"). The above mentioned values might be different in other PCT assays, if these have been calibrated differently from BRAHMS KRYPTOR PCT sensitive. The above mentioned values shall apply for such differently calibrated PCT assays accordingly, taking into account the differences in calibration. One possibility of quantifying the difference in calibration is a method comparison analysis (correlation) of the PCT assay in question with the BRAHMS KRYPTOR PCT sensitive by measuring PCT in samples using both methods. Another possibility is to determine with the PCT assay in question, given this test has sufficient analytical sensitivity, the median PCT level of a representative normal population, compare results with the median PCT levels as described in EP 09011073.5 ("Procalcitonin for the prognosis of adverse events in the asymptomatic population") and recalculate the calibration based on the difference obtained by this comparison.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy) and "disease" populations (i.e. patients suffering from diabetes, insulin resistance and/or metabolic syndrome). For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art (See, e.g., Hanley et al. 1982. Radiology 143: 29-36). Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition (e.g. prognosis). Thus, the area under the ROC curve can be used to determine the effectiveness of the test.

In certain embodiments, markers and/or marker panels are selected to exhibit at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In particularly preferred embodiments, both the sensitivity and specificity are at least about 75%, more preferably at least about 80%, even more preferably at least about 85%, still more preferably at least about 90%, and most preferably at least about 95%. The term "about" in this context refers to +/−5% of a given measurement.

Threshold levels can be obtained for instance from a Kaplan-Meier analysis, where the occurrence of a disease or the probability of an adverse outcome and/or death is correlated with the e.g. quintiles of the respective markers in the population. According to this analysis, subjects with marker levels above the 80th percentile have a significantly increased risk for getting an adverse event according to the invention. This result is further supported by Cox regression analysis with adjustment for classical risk factors. The highest quartile versus all other subjects is highly significantly associated with increased risk for getting a disease or the probability of an adverse outcome and/or death according to the invention.

Other preferred cut-off values are for instance the 90th, 95th or 99th percentile of a reference population. By using a higher percentile than the 80th percentile, one reduces the number of false positive subjects identified, but one might miss to identify subjects, who are at moderate, albeit still increased risk. Thus, one might adapt the cut-off value depending on whether it is considered more appropriate to identify most of the subjects at risk at the expense of also identifying "false positives", or whether it is considered more appropriate to identify mainly the subjects at high risk at the expense of missing several subjects at moderate risk.

Other mathematical possibilities to calculate an individual's risk by using the individual's marker level value and other prognostic laboratory and clinical parameters are for instance the NRI (Net Reclassification Index) or the IDI (Integrated Discrimination Index). The indices can be calculated according to Pencina (Pencina M J, et al.: *Evaluating the added predictive ability of a new marker: from area under the ROC curve to reclassification and beyond. Stat Med.* 2008; 27:157-172).

The preferred detection methods comprise immunoassays in various formats such as for instance radioimmunoassay (RIA), chemiluminescence and fluorescence-immunoassays, Enzyme-linked immunoassays (ELISA), Luminex® based bead arrays, protein microarray assays, and rapid test formats such as for instance immunochromatographic strip tests.

The assays can be homogenous or heterogeneous assays, competitive and non-competitive assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person (*The Immunoassay Handbook*, Ed. David Wild, Elsevier LTD, Oxford; 3rd ed. (May 2005), ISBN-13: 978-0080445267; Hultschig C et al., *Curr Opin Chem Biol.* 2006 February; 10(1):4-10. PMID: 16376134, incorporated herein by reference).

In a particularly preferred embodiment the assay comprises two capture molecules, preferably antibodies which are both present as dispersions in a liquid reaction mixture, wherein a first labelling component is attached to the first capture molecule, wherein said first labelling component is part of a labelling system based on fluorescence- or chemiluminescence-quenching or amplification, and a second labelling component of said marking system is attached to the second capture molecule, so that upon binding of both capture molecules to the analyte a measurable signal is generated that allows for the detection of the formed sandwich complexes in the solution comprising the sample.

Even more preferred, said labeling system comprises rare earth cryptates or rare earth chelates in combination with fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), RHODAMINE, RHODAMINE GREEN, RHODAMINE RED, RHODAMINE 110, BODIPY dyes, such as BODIPY TMR, Oregon Green, Coumarines such as Umbelliferone, Benzimides, such as Hoechst 33258; Phenanthridines, such as TEXAS RED, YAKIMA YELLOW, ALEXA FLUOR, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, *Encyclopedia of chemical technology*, 4$^{th}$ ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridiniumesters.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8$ M$^{-1}$.

In the context of the present invention, "capture molecules" are molecules which may be used to bind target molecules or molecules of interest, i.e. analytes (i.e. in the context of the present invention PCT and fragments thereof), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules may for instance be selected from the group comprising a nucleic acid molecule, a carbohydrate molecule, a peptide nucleic acid (PNA) molecule, a protein, an antibody, a peptide or a glycoprotein. Preferably, the capture molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

In a preferred embodiment of the invention procalcitonin or fragments thereof of at least 12 amino acids in length is used for antibiotic guidance in patients with stable chronic heart failure or patients being suspected of having stable chronic heart failure having an increased risk of getting an adverse event.

It is even more preferred that an antibiotic is administered when the level of procalcitonin or fragments thereof of at least 12 amino acids in length in a sample of a bodily fluid of a patient with stable chronic heart failure or a patient being suspected of having stable chronic heart failure is between 0.015 and 0.05 ng/ml, more preferred between 0.015 ng/mL and 0.035 ng/mL, even more preferred between 0.015 ng/mL and 0.03 ng/mL, even more preferred between 0.015 ng/mL and 0.025 ng/mL, most preferred between 0.02 ng/mL and (below) 0.015 ng/mL.

It is even more preferred that an antibiotic is administered when the level of procalcitonin or fragments thereof of at least 12 amino acids in length in a sample of a bodily fluid of a patient with stable chronic heart failure or a patient being suspected of having stable chronic heart failure is higher than 0.05 ng/mL, preferably higher than 0.035 ng/mL, more preferably higher than 0.03 ng/mL, even more preferably higher than 0.025 ng/mL, even more preferably higher than 0.02 ng/mL, most preferred higher than 0.015 ng/mL.

EXAMPLES

Example 1

Study Population and Procedures

Patients enrolled were consecutive referrals to a community-based CHF program in Kingston-upon-Hull and the East Riding of Yorkshire, UK, serving a population of 600 000 people between August 2001 and June 2009. Patients with suspected stable chronic heart failure were referred from the local community to a specialist clinic for the diagnosis and management of possible stable chronic heart failure and were invited to participate. Consenting patients underwent a systematic evaluation including prior medical history, medications, symptoms, signs, electro- and echocardiograms, standard hematology and biochemistry profiles and measurement of PCT and amino-terminal pro-brain natriuretic peptide (NT-proBNP).

Results

Of 1891 patients enrolled, the median age was 72 years (interquartile range [IQR]: 64 to 78), 669 were women, 807 had left ventricular systolic dysfunction (LVSD), 400 had no major echocardiographic abnormalities other than LVSD, 192 had no major echo abnormality but an NT-proBNP>400 ng/L (of whom 65 had atrial fibrillation and 15 had eGFR <30 ml/min) and 492 had none of the above. Median (IQR) PCT overall was 0.022 (0.017-0.047) ng/mL and for each of the four sub-groups was 0.023 (0.018-0.032), 0.022 (0.017-0.031), 0.024 (0.019-0.035) and 0.020 (0.016-0.025) ng/mL respectively. Over a median follow-up of 5.0 (IQR: 3.4-7.1) years, 783 (41.8%) patients died, 447 of cardiovascular causes. In univariable analysis, log (PCT) was strongly related to all-cause, cardiovascular and non-cardiovascular mortality (Hazard Ratio [HR]: 1.91 with 95% CI: (1.73-2.11), HR: 1.94 (1.71-2.21) and HR: 1.89 (1.61-2.22) respectively, p<0.001 for all). The HR for all-cause mortality by PCT quintiles for univariate Cox-regression analysis (unadjusted and adjusted for age and gender) are shown in Table 3. In a multi-variable Cox-regression model, PCT provided additional prognostic information to 17 standard clinical variables (age, sex, etiology, diabetes, COPD, symptoms, quality of life, NYHA, BMI, heart rate and rhythm, systolic blood pressure, edema, severity of ventricular dysfunction, hemoglobin and creatinine and NT-proBNP) for all-cause mortality.

Example 2

Study Population and Procedures

Further to the patients enrolled in Example 1,651 additional patients with suspected stable chronic heart failure were included into the study. Again, these patients who signed a consent to participate in the study, underwent a systematic evaluation including prior medical history, medications, symptoms, signs, electro- and echocardiograms, standard hematology and biochemistry profiles and measurement of PCT and amino-terminal pro-brain natriuretic peptide (NT-proBNP).

Results

Figure 1:
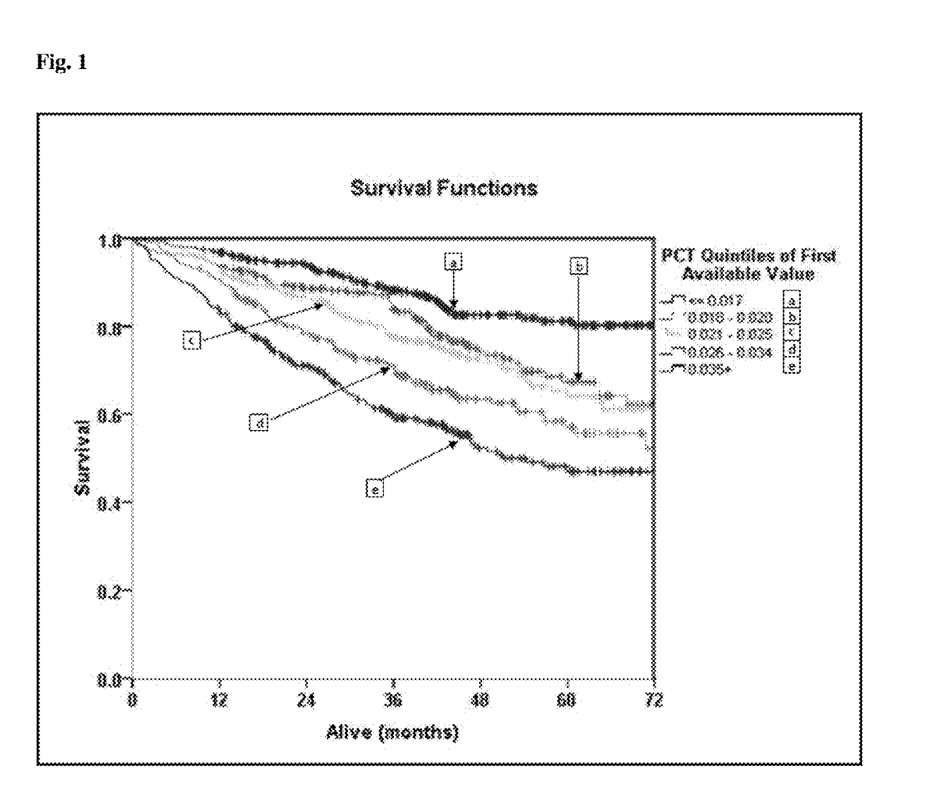
FIG. 1: Kaplan-Meier survival curves by quintiles of PCT for patients with stable chronic heart failure or being suspected of having stable chronic heart failure (prediction of mortality).
Figure 2:
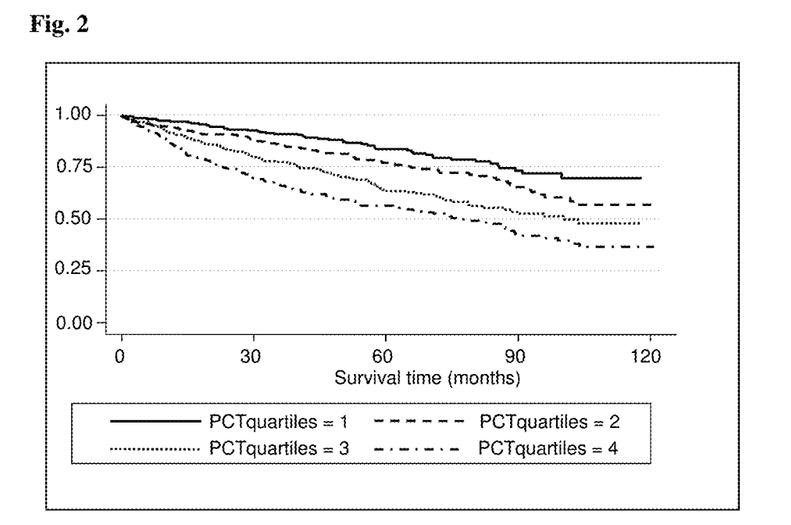
FIG. 2: Kaplan-Meier survival curves for prognosis of patients with LVSD according to quartiles of PCT (all-cause mortality).
Figure 3:
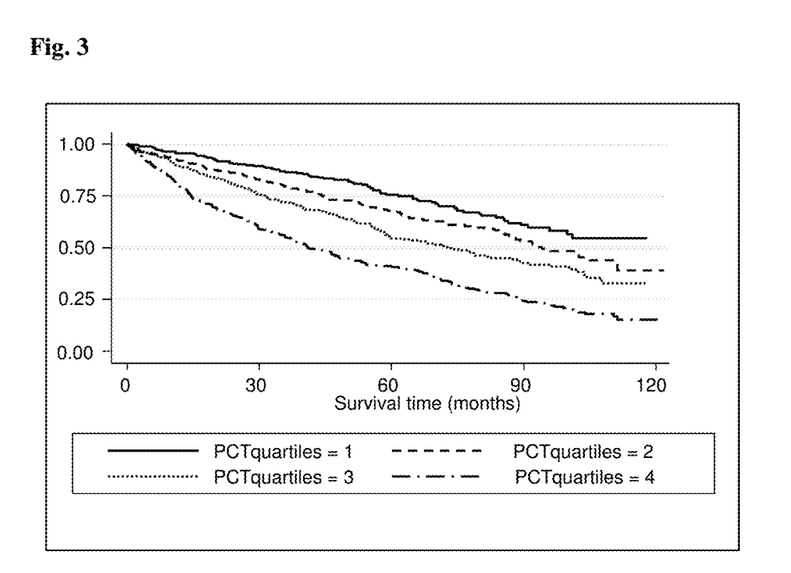
FIG. 3: Kaplan-Meier survival curves for prognosis of patients with LVSD according to quartiles of PCT (cardiovascular mortality).
Figure 4:
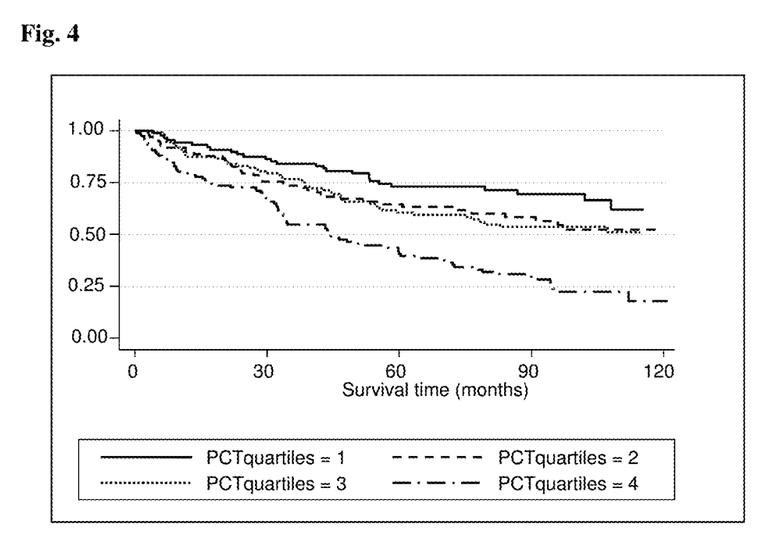
FIG. 4: Kaplan-Meier survival curves for prognosis of patients with MSHD according to quartiles of PCT (all-cause mortality).
Figure 5:
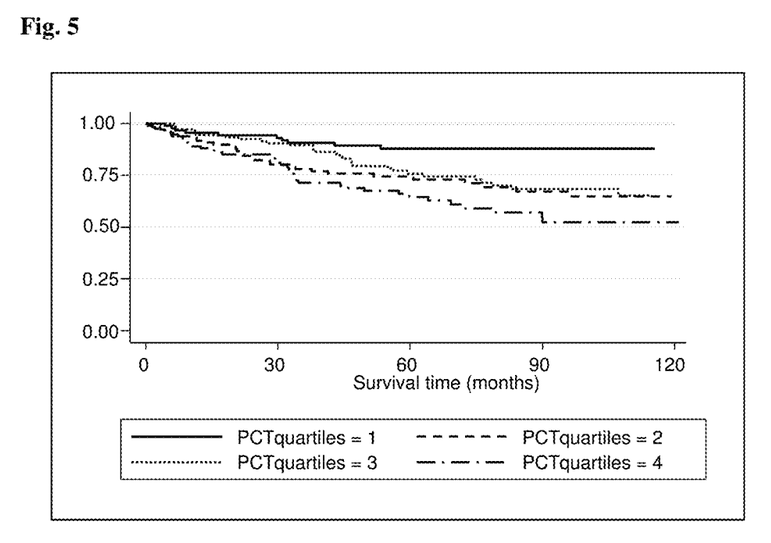
FIG. 5: Kaplan-Meier survival curves for prognosis of patients with MSHD according to quartiles of PCT (cardiovascular mortality).
Figure 6:
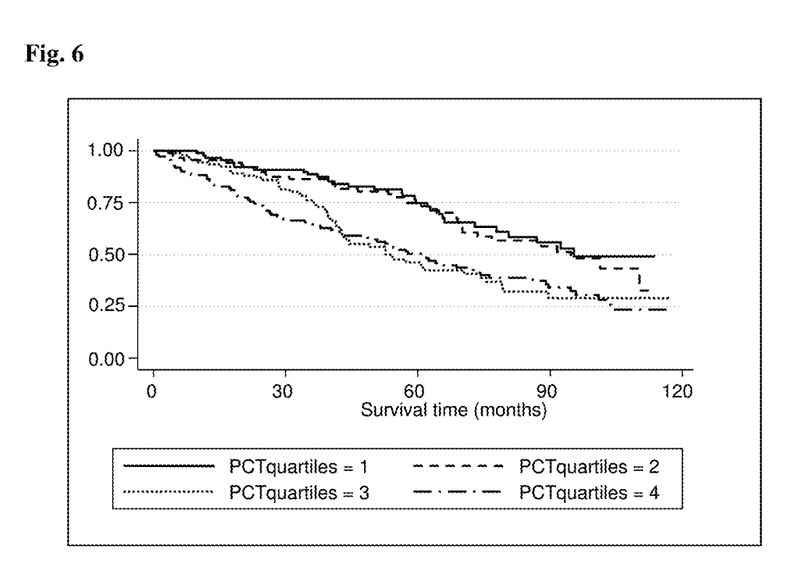
FIG. 6: Kaplan-Meier survival curves for prognosis of patients without MSHD but with atrial fibrillation or N-terminal-proBNP (NT-proBNP)>400 ng/L according to quartiles of PCT (all-cause mortality).
Figure 7:
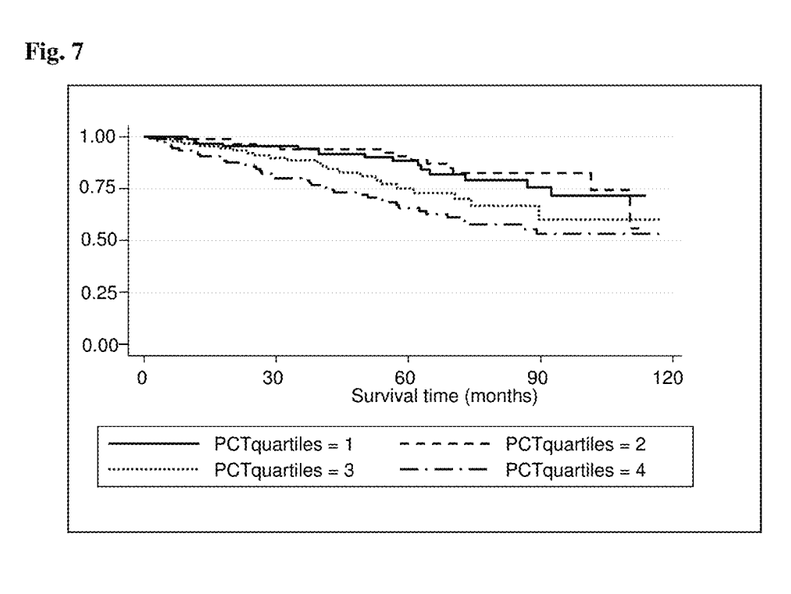
FIG. 7: Kaplan-Meier survival curves for prognosis of patients without MSHD but with atrial fibrillation or N-terminal-proBNP (NT-proBNP)>400 ng/L according to quartiles of PCT (cardiovascular mortality).
Figure 8:
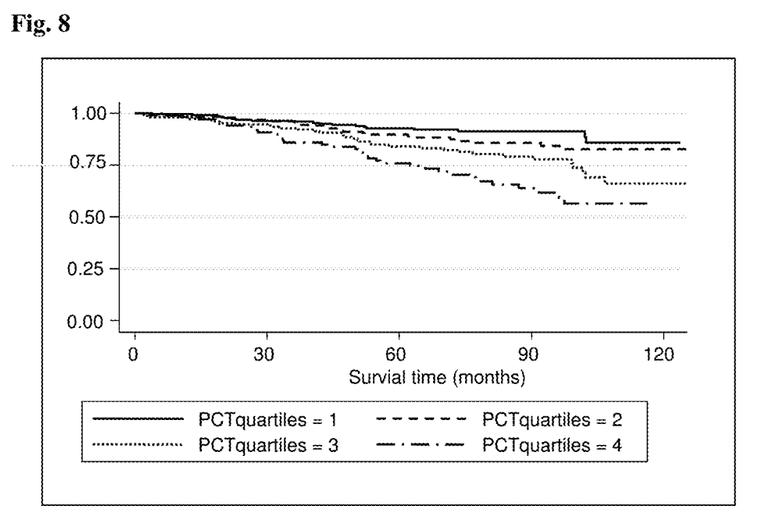
FIG. 8: Kaplan-Meier survival curves for prognosis of patients in sinus rhythm and N-terminal-proBNP (NT-proBNP)<400 ng/L according to quartiles of PCT (all-cause mortality).
Figure 9:
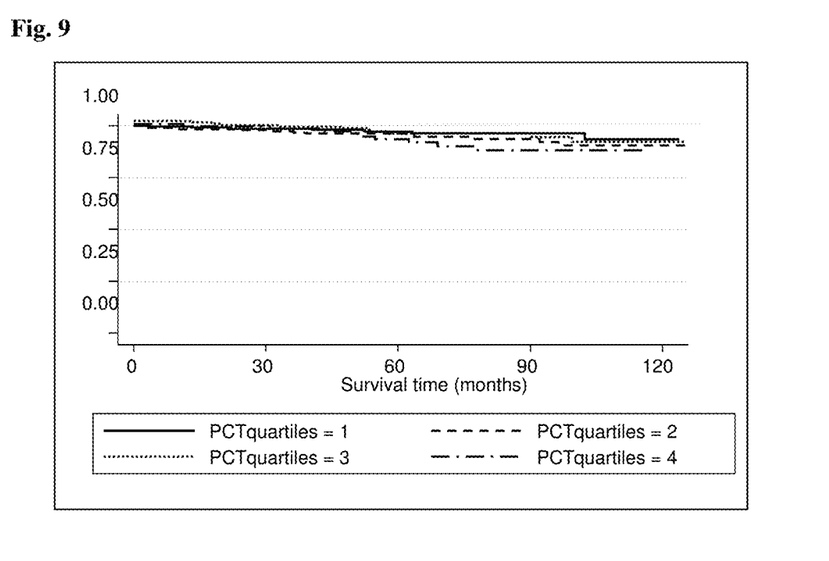
FIG. 9: Kaplan-Meier survival curves for prognosis of patients in sinus rhythm and N-terminal-proBNP (NT-proBNP)<400 ng/L according to quartiles of PCT (cardiovascular mortality).

Of 2542 patients enrolled in total, 1100 had left ventricular systolic dysfunction (LVSD). Out of 1442 patients with no LVSD n=415 patients had major structural heart disease (MSHD). Patient characteristics were described by quartiles of plasma PCT (Table 4) and by top and bottom decile to show impact of extreme values. Variables are shown as percentages or median and inter-quartile range. Simple and multiple linear regression models were used to identify independent variables associated with an inverse transformation of PCT (Table 5). Predictors of all-cause mortality (with and without PCT included) are shown in Table 6. Patients with events, Hazard Ratio for the highest versus lowest quartile of PCT and C-statistics are summarized in Table 7. Kaplan-Meier curves were used to compare survival probabilities of specified outcomes (all-cause mortality, cardiovascular mortality) by phenotypes (patients with LVSD, MSHD, without MSHD but with atrial fibrillation or NT-proBNP>400 ng/L, and patients in sinus rhythm and NT-proBNP <400 ng/L, respectively) (FIG. 2 to 9).

Again PCT was strongly related to all-cause and cardiovascular mortality (unadjusted Hazard Ratio [HR]: 3.46 with 95% CI: (2.63-4.56) and HR: 3.72 (2.58-5.35) respectively, p<0.001 for both). On multivariable analysis, higher plasma PCT concentrations are associated with worse renal function, greater age, ischaemic heart disease and with markers of more severe heart failure but not other markers of infection or inflammation such as High Sensitivity C-Reactive Protein (hsCRP) or white cell count. Amongst patients with LVSD, PCT predicts all-cause and cardiovascular mortality, especially heart failure deaths, independently of other prognostic markers including NT-proBNP. PCT also predicts mortality in patients without LVSD, including patients in whom the diagnosis of heart failure has been refuted but this appears to be mainly non-cardiovascular.

TABLE 1

Classification of Heart failure (according to the ESC Guidelines, 2008)

| Classification | Definition |
|---|---|
| New onset (first presentation) | Acute or slow onset |
| Transient | Recurrent or episodic |
| Chronic (persistent) | Stable, worsening or decompensated |

TABLE 2

Comparison of acute and chronic heart failure

| | Acute HF | | |
|---|---|---|---|
| Feature | New onset HF | Acute decompensated HF | Stable chronic HF |
| Symptom severity | Marked | Marked | Mild to moderate |
| Pulmonary edema | Frequent | Frequent | Rare |
| Peripheral edema | Rare | Frequent | Frequent |
| Weight gain | Non to mild | Marked | Frequent |
| Total body volume | No or mild increase | Markedly increased | Increased |
| Cardiac hypertrophy | Uncommon | Common | Common |
| Wall stress | Elevated | Markedly elevated | Elevated |
| Acute ischemia | Common | Occasional | Rare |
| Hypertensive crisis | Common | Occasional | Rare |

TABLE 3

HR for all-cause mortality by PCT quintiles for univariate Cox-regression analysis

| PCT in ng/mL (Quintile) | HR (unadjusted) | HR (adjusted by age and gender) |
|---|---|---|
| 0.018-0.020 ($2^{nd}$) | 1.789 | 1.673 |
| >0.020-0.025 ($3^{rd}$) | 2.018 | 1.661 |
| >0.025-0.035 ($4^{th}$) | 2.826 | 2.359 |
| >0.035 ($5^{th}$) | 3.905 | 2.995 |

TABLE 4

Patient characteristics according to quantiles of PCT

| | Lowest Decile | Lowest Quartile | Quartile 2 | Quartile 3 | Highest Quartile | Highest Decile |
|---|---|---|---|---|---|---|
| N | 254 | 635 | 636 | 636 | 635 | 254 |
| PCT (pg/ml) | 13 (12-14) | 15 (13-16) | 19 (18-21) | 25 (23-28) | 43 (35-62) | 69 (54-94) |
| Age (years) | 66 (58-74) | 69 (60-7) | 71 (63-77) | 73 (66-79) | 75 (68-80) | 75 (68-81) |
| Men (%) | 143 (56%) | 372 (59%) | 402 (63%) | 423 (67%) | 420 (66%) | 160 (63%) |
| IHD (%) | 124 (49%) | 324 (51%) | 323 (51%) | 332 (53%) | 328 (52%) | 112 (45%) |
| DM (%) | 32 (14%) | 98 (17%) | 110 (18%) | 104 (18%) | 154 (27%) | 66 (29%) |
| COPD (%) | 19 (8%) | 55 (9%) | 62 (10%) | 76 (12%) | 67 (11%) | 32 (13%) |
| NYHA (III/IV) (%) | 43 (17%) | 105 (17%) | 146 (23%) | 159 (25%) | 210 (33%) | 86 (34%) |
| SOB ADL Severe (%) | 29 (11%) | 67 (11%) | 95 (15%) | 115 (18%) | 138 (22%) | 61 (24%) |
| edema > mild (%) | 6 (2%) | 24 (4%) | 18 (3%) | 28 (4%) | 47 (7%) | 24 (9%) |

TABLE 4-continued

Patient characteristics according to quantiles of PCT

|  | Lowest Decile | Lowest Quartile | Quartile 2 | Quartile 3 | Highest Quartile | Highest Decile |
|---|---|---|---|---|---|---|
| Poor Overall Health | 45 (18%) | 110 (17%) | 129 (20%) | 147 (23%) | 188 (30%) | 87 (34%) |
| Loop diuretic (%) | 114 (46%) | 312 (50%) | 367 (59%) | 414 (67%) | 497 (80%) | 204 (81%) |
| BMI (kg/m$^2$) | 27.4 (24.0-31.3) | 27.8 (24.5-31.4) | 28.2 (24.9-31.6) | 27.9 (25.0-31.9) | 28.3 (25.1-32.2) | 28.2 (25.1-32.4) |
| HR (bpm) | 67 (60-76) | 67 (59-77) | 69 (59-80) | 70 (60-84) | 75 (63-88) | 78 (64-90) |
| SBP (mmHg) | 137 (120-156) | 139 (122-156) | 140 (124-158) | 138 (120-154) | 133 (116-155) | 132 (113-154) |
| Sinus Rhythm (%) | 195 (77%) | 487 (77%) | 470 (74%) | 454 (71%) | 403 (64%) | 161 (63%) |
| QRS (msec) | 96 (86-110) | 98 (86-116) | 100 (88-124) | 102 (88-122) | 102 (90-130) | 102 (88-126) |
| LA diam/BSA (cm/m$^2$) | 2.0 (1.8-2.3) | 2.0 (1.8-2.3) | 2.1 (1.8-2.4) | 2.1 (1.8-2.4) | 2.2 (1.9-2.5) | 2.2 (2.0-2.6) |
| LVEDD/BSA (cm/m$^2$) | 2.7 (2.4-3.1) | 2.8 (2.4-3.2) | 2.9 (2.5-3.3) | 2.9 (2.5-3.3) | 2.9 (2.5-3.3) | 3.0 (2.6-3.4) |
| MR > mild (%) | 55 (22%) | 129 (20%) | 146 (23%) | 128 (20%) | 201 (32%) | 86 (34%) |
| Hb (g/dL) | 13.7 (12.7-14.5) | 13.7 (12.8-14.6) | 13.5 (12.5-14.6) | 13.5 (12.4-14.7) | 12.9 (11.0-14.1) | 12.5 (11.2-13.9) |
| WBCC (x10$^9$/L) | 6.8 (5.7-7.9) | 6.6 (5.6-7.9) | 6.8 (5.8-8.1) | 7.1 (5.8-8.4) | 7.4 (6.0-8.8) | 7.6 (6.1-8.9) |
| hsCRP (mg/L) | 2.1 (0.8-4.7) | 2.5 (1.0-4.8) | 3.1 (1.6-6.0) | 4.5 (2.1-8.0) | 6.9 (3.4-15.0) | 9.3 (4.2-29.0) |
| Sodium (mmol/L) | 139 (137-140) | 139 (137-141) | 139 (137-141) | 139 (138-141) | 139 (136-141) | 138 (136-141) |
| Urea (mmol/L) | 5.1 (4.0-6.3) | 5.4 (4.4-6.5) | 5.9 (4.8-7.4) | 6.9 (5.4-8.9) | 8.9 (6.2-14.0) | 10.1 (6.8-16.0) |
| Creatinine (μmol/L) | 83 (72-98) | 87 (75-101) | 94 (81-111) | 104 (88-127) | 127 (99-171) | 136 (102-195) |
| eGFR (ml/min/1.73 m$^2$) | 76 (65-88) | 73 (61-85) | 66 (56-80) | 60 (47-72) | 48 (33-62) | 41 (28-58) |
| Cholesterol (mmol/L) | 4.5 (3.9-5.4) | 4.6 (3.8-5.5) | 4.6 (4.0-5.6) | 4.6 (3.9-5.6) | 4.6 (3.8-5.5) | 4.4 (3.8-5.5) |
| ALT (iu/L) | 20 (17-26) | 20 (17-26) | 21 (17-27) | 21 (17-28) | 21 (17-29) | 22 (16-33) |
| Alk Phos (iu/L) | 68 (58-84) | 69 (57-85) | 71 (59-87) | 72 (59-88) | 76 (63-99) | 83 (65-107) |
| Albumin (g/L) | 38 (27-40) | 38 (37-40) | 38 (36-40) | 38 (36-40) | 36 (34-39) | 36 (32-39) |
| NT-proBNP (ng/L) | 438 (144-1166) | 456 (136-1198) | 627 (173-1593) | 766 (196-2056) | 1,662 (505-4262) | 2,017 (632-5734) |

TABLE 5

Predictors of plasma PCT (inverse transformation) on multi-variable analysis

|  | Coefficient | 95% CI | SE | t | p | Correlation (R$^2$) |
|---|---|---|---|---|---|---|
| Log (creatinine) | −22.039 | (−24.21 −19.86) | 1.107 | −19.89 | <0.001 | −0.46 (p < 0.001) |
| Heart Rate (bpm) | −0.139 | (−0.179 −0.099) | 0.020 | −6.82 | <0.001 | −0.16 (p < 0.001) |
| Age (years) | −0.193 | (−0.264 −0.122) | 0.036 | −5.34 | <0.001 | −0.24 (p < 0.001) |
| Edema severity |  |  |  | 5.11 | 0.006 | −0.16 (p < 0.001) |
| Mild | −2.435 | (−4.03 −0.834) | 0.816 | −2.98 | 0.003 |  |
| Severe | −2.784 | (−5.94 0.376) | 1.61 | −1.73 | 0.084 |  |
| Body Mass Index | −0.1856 | (−0.308, −0.062) | 0.062 | −2.95 | 0.003 | −0.03 (p = 0.087) |
| Ischaemic Heart Disease | 2.020 | (0.625, 3.414) | 0.711 | 2.84 | 0.005 | −0.01 (p = 0.659) |
| Log (NT-proBNP) | −0.780 | (−1.375, −0.186) | 0.303 | −2.57 | 0.010 | −0.28 (p < 0.001) |

TABLE 6

Predictors of All-Cause Mortality
(with and without Procalcitonin excluded)

| Variable | With Procalcitonin | | Without Procalcitonin | |
|---|---|---|---|---|
|  | t | HR | t | HR |
| Age (per decade) | 11.79 | 1.77 (1.61-1.95) | 11.56 | 1.76 (1.60-1.94) |
| Log (NT-proBNP) | 9.65 | 1.34 (1.27-1.43) | 10.08 | 1.36 (1.28-1.45) |
| Log (PCT) | 5.38 | 1.33 (1.19-1.47) | — | — |
| COPD | 4.69 | 1.54 (1.28-1.84) | 4.87 | 1.56 (1.31-1.87) |
| NYHA (I-II/III-IV) | 4.14 | 1.36 (1.17-1.57) | 4.15 | 1.36 (1.17-1.57) |
| Diabetes Mellitus | 3.54 | 1.32 (1.13-1.55) | 3.26 | 1.29 (1.11-1.51) |

TABLE 6-continued

Predictors of All-Cause Mortality
(with and without Procalcitonin excluded)

| | With Procalcitonin | | Without Procalcitonin | |
|---|---|---|---|---|
| Variable | t | HR | t | HR |
| Women | −2.71 | 0.82 (0.71-0.95) | −2.40 | 0.84 (0.73-0.97) |
| Hemoglobin (g/dL) | −2.33 | 0.95 (0.91-0.99) | −2.47 | 0.95 (0.91-0.99) |
| Breathlessness on ADL | 3.10 | | 2.77 | |
| Some | 0.24 | 1.02 (0.86-1.22) | 0.38 | 1.04 (0.87-1.23) |
| A lot | 2.09 | 1.23 (1.01-1.49) | 2.06 | 1.23 (1.05-1.59) |
| Self-Rating of Overall health | 2.53 | | 2.91 | |
| Average | 1.28 | 1.11 (0.95-1.31) | 1.33 | 1.12 (0.96-1.32) |
| Poor | 2.27 | 1.27 (1.03-1.56) | 2.43 | 1.29 (1.06-1.59) |
| Log (creatinine) | 1.98 | 1.23 (1.00-1.52) | 4.50 | 1.55 (1.28-1.29) |

TABLE 7

Patients with events, Hazard Ratio for the highest v. lowest Quartile of Procalcitonin and C-Statistic

| | Overall | LVSD | Other MSHD or Not SR or NT-proBNP >400 ng/L | No MSHD/ SR/NT-proBNP <400 ng/L |
|---|---|---|---|---|
| N = | 2,542 | 1,100 | 793 | 649 |
| Numbers of Patients with an Event within next 3 years | | | | |
| All-Cause Mortality | 549 | 306 | 202 | 41 |
| Cardiovascular Mortality | 338 | 214 | 110 | 14 |
| Heart Failure Death | 82 | 57 | 25 | 0 |
| Non-CV Death | 200 | 87 | 89 | 24 |
| Cancer Death | 63 | 34 | 17 | 12 |
| Hazard Ratios - Unadjusted and Adjusted for Sex and Variables in Table 4 | | | | |
| All-Cause Mortality | 3.46 (2.63-4.56) | 3.41 (2.32-5.01) | 3.09 (1.97-4.85) | 2.56 (1.09-6.03) |
| | 1.97 (1.47-2.65) | 2.18 (1.44-3.29) | 1.69 (1.04-2.77) | 1.98 (0.74-5.26) |
| Cardiovascular Mortality | 3.72 (2.58-5.35) | 3.69 (2.28-5.96) | 3.60 (1.66-5.64) | 1.22 (0.20-7.52) |
| | 1.91 (1.29-2.82) | 2.28 (1.37-3.81) | 1.49 (0.76-2.92) | 0.57 (0.07-4.96) |
| Heart Failure Death | 7.05 (2.76-17.98) | 22.36 (3.02-165.53) | 2.24 (0.72-6.96) | — |
| | 2.39 (0.89-6.41) | 9.43 (1.24-71.90) | 1.25 (0.34-4.62) | |
| Non-CV Death | 3.15 (2.05-4.83) | 2.67 (1.38-5.15) | 3.53 (1.77-7.05) | 1.84 (0.95-3.96) |
| | 2.06 (1.29-3.27) | 1.84 (0.90-3.75) | 2.27 (1.08-4.75) | 2.77 (0.85-8.97) |
| C-Statistic | | | | |
| All-Cause Mortality | 0.695 | 0.668 | 0.680 | 0.709 |
| Cardiovascular Mortality | 0.688 | 0.666 | 0.684 | 0.638 |
| Heart Failure Death | 0.740 | 0.730 | 0.777 | — |
| Non-CV Death | 0.713 | 0.678 | 0.699 | 0.708 |

Sequences

SEQ ID NO: 1 (amino acid sequence of PCT):
  1  APFRSALESS PADPATLSED EARLLLAALV QDYVQMKASE LEQEQEREGS

51  SLDSPRSKRC GNLSTCMLGT YTQDFNKFHT FPQTAIGVGA PGKKRDMSSD

101  LERDHRPHVS MPQNAN

SEQ ID NO: 2 (amino acid sequence of NT-pro-BNP):
  1  HPLGSPGSAS DLETSGLQEQ RNHLQGKLSE LQVEQTSLEP LQESPRPTGV

51  WKSREVATEG IRGHRKMVLY TLRAPR

SEQ ID NO: 3 (amino acid sequence of BNP):
  1  SPKMVQGSGC FGRKMDRISS SSGLGCKVLR RH

The invention claimed is:

1. A method for determining an enhanced risk of a patient with stable chronic heart failure or suspected of having stable chronic heart failure suffering an adverse event, comprising:
   (a) detecting and quantitating the level of procalcitonin (PCT), or a fragment thereof consisting of amino acids 1 to 116 or 2 to 116 or 3 to 116 of SEQ ID NO:1, in a sample of bodily fluid of said patient, wherein the detection and quantitation comprises a PCT detection assay wherein the sample is contacted with an antibody that specifically binds to PCT to form a detectable PCT:antibody complex, and detecting and quantitating the complex; and
   (b) comparing said level of PCT or fragments thereof to a statistically significant predetermined threshold level, wherein, when said level of procalcitonin or fragments thereof exceeds said threshold level, said patient is determined to have an enhanced risk of suffering an adverse event.

2. The method of claim 1, wherein the adverse event is selected from the group consisting of worsening or decompensation of heart failure, a cerebrovascular event, a cardiovascular event and mortality.

3. The method of claim 1, further comprising correlating said level of procalcitonin or fragments thereof with one or more clinical variables selected from a the group consisting of age, gender, diabetes, COPD (chronic obstructive pulmonary disease), symptoms, quality of life, NYHA (New York Heart Association functional classification of heart failure category), BMI (body mass index), heart rate and rhythm, systolic and diastolic blood pressure, edema and severity of ventricular dysfunction.

4. The method of claim 1, wherein the PCT assay has a lower detection limit below 0.05 ng/mL.

5. The method of claim 1, wherein said patient does not have acute or decompensated heart failure.

6. The method of claim 1, wherein said sample is selected from the group consisting of a blood sample, a serum sample, and a plasma sample.

7. The method of claim 1, wherein said threshold level is between 0.015 and 0.05 ng/ml, inclusive.

8. The method of claim 7, wherein said threshold level is between 0.015 ng/mL and 0.035 ng/mL, inclusive.

9. The method of claim 1, wherein the determination of an enhanced risk relates to the enhanced risk of suffering an adverse event within 7 years.

10. The method of claim 9, wherein the determination of an enhanced risk relates to the enhanced risk of suffering an adverse event within 5 years.

11. The method of claim 9, wherein the determination of an enhanced risk relates to the enhanced risk of suffering an adverse event within 4 years.

12. The method of claim 9, wherein the determination of an enhanced risk relates to the enhanced risk of suffering an adverse event within 2 years.

13. The method of claim 1, further comprising correlating said level of procalcitonin or fragments thereof with the level of one or more additional prognostic marker(s), wherein the combination of said level of procalcitonin or fragments thereof with said level of additional prognostic marker(s) increases the predictive value of said level of procalcitonin or fragments thereof or the level of said related marker for getting an adverse event.

14. The method of claim 13, wherein the additional prognostic marker is selected from a group consisting of troponin, myeloperoxidase, CRP (C-reactive protein), neopterin, GDF-15 (growth-differentiation factor 15), ST2 (interleukin-1 receptor-like protein ST2), cystatin-C, haemoglobin, creatinine and the following peptides in form of their mature peptides, precursors, pro-hormones and associated prohormone fragments: natriuretic peptides, adrenomedullin, endothelins, and vasopressin.

15. The method of claim 14, wherein one of said prognostic marker(s) is pre-proBNP (pre-pro-B-type natriuretic peptide) or fragments thereof in a sample obtained from said patient.

16. A method for antibiotic treatment guidance in a patient with stable chronic heart failure or suspected of having stable chronic heart failure, said patient having an increased risk of suffering an adverse event, comprising:
   (a) detecting and quantitating the level of procalcitonin (PCT), or a fragment thereof consisting of amino acids 1 to 116 or 2 to 116 or 3 to 116 of SEQ ID NO:1, in a sample of bodily fluid of said patient, wherein the detection and quantitation comprises a PCT detection assay wherein the sample is contacted with an antibody that specifically binds to PCT to form a detectable PCT:antibody complex, and detecting and quantitating the complex; and
   (b) comparing said level of PCT or fragments thereof to a statistically significant predetermined threshold level, wherein, when said level of procalcitonin or fragments thereof exceeds said threshold level, said patient is determined to have an enhanced risk of suffering an adverse event, and the need for antibiotic treatment is indicated.

17. The method of claim 16, further comprising administering an antibiotic when the level of PCT or fragments thereof of at least 12 amino acids in length in a sample of a bodily fluid of a patient with stable chronic heart failure or suspected of having stable chronic heart failure is between 0.015 and 0.05 ng/ml, inclusive.

18. The method of claim 1, wherein (a) includes detecting and quantitating the level of a fragment of PCT consisting of amino acids 2 to 116 or 3 to 116 of SEQ ID NO:1, in a sample of bodily fluid of said patient, wherein the detection and quantitation comprises a PCT detection assay wherein the sample is contacted with an antibody that specifically binds to PCT to form a detectable PCT:antibody complex, and detecting and quantitating the complex.

19. The method of claim 16, wherein (a) includes detecting and quantitating the level of a fragment of PCT consisting of amino acids 2 to 116 or 3 to 116 of SEQ ID NO:1, in a sample of bodily fluid of said patient, wherein the detection and quantitation comprises a PCT detection assay wherein the sample is contacted with an antibody that specifically binds to PCT to form a detectable PCT:antibody complex, and detecting and quantitating the complex.

20. The method of claim 14, wherein one of said prognostic marker(s) is NT pro-BNP (SEQ ID NO:2) or BNP (SEQ ID NO:3).

* * * * *